US00PP34089P2

(12) United States Plant Patent
Zale

(10) Patent No.: US PP34,089 P2
(45) Date of Patent: Apr. 5, 2022

(54) ***MAGNOLIA* TREE NAMED 'BOONEARB'**

(50) Latin Name: *Magnolia grandiflora*
Varietal Denomination: BooneArb

(71) Applicant: FRIENDS of BOONE COUNTY ARBORETUM, Union, KY (US)

(72) Inventor: Peter Zale, Kennett Square, PA (US)

(73) Assignee: FRIENDS of BOONE COUNTY ARBORETUM, Union, KY (US)

( * ) Notice: Subject to any disclaimer, the term of this patent is extended or adjusted under 35 U.S.C. 154(b) by 0 days.

(21) Appl. No.: 17/233,515

(22) Filed: Apr. 18, 2021

(51) Int. Cl.
*A01H 5/00* (2018.01)
*A01H 6/00* (2018.01)

(52) U.S. Cl.
USPC ..... Plt./223

(58) Field of Classification Search
USPC ..... Plt./216, 223
See application file for complete search history.

*Primary Examiner* — Susan McCormick Ewoldt
(74) *Attorney, Agent, or Firm* — C. Anne Whealy

(57) ABSTRACT

A new and distinct cultivar of *Magnolia* tree named 'BooneArb', characterized by its upright and uniformly pyramidal tree form; freely branching habit with numerous lateral branches providing a full and densely foliated appearance; large glossy dark green-colored leaves; large white-colored flowers that are highly fragrant; good landscape performance and superior cold hardiness.

4 Drawing Sheets

Figure 1:
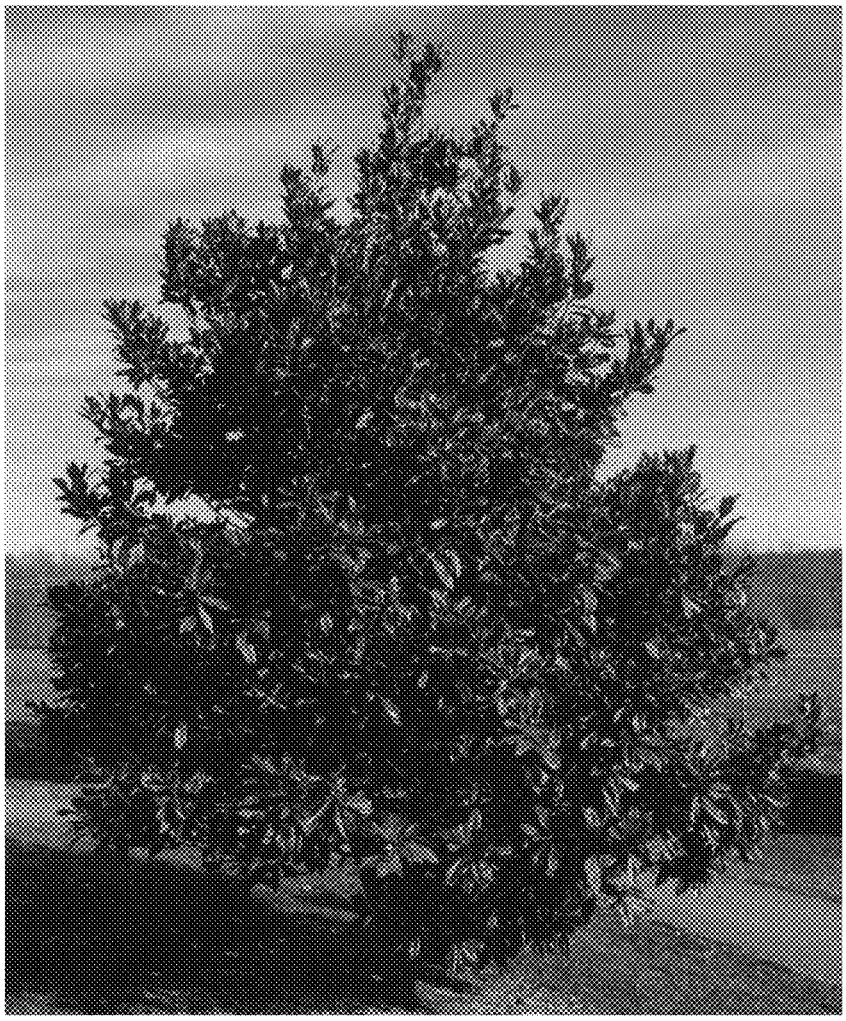

Botanical designation: *Magnolia grandiflora.*
Cultivar denomination: 'BooneArb'.

STATEMENT REGARDING PRIOR DISCLOSURES BY INVENTOR & APPLICANT/ASSIGNEE

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Magnolia* tree, botanically known as *Magnolia grandiflora*, commercially referred to as Southern *Magnolia* and hereinafter referred to by the name 'BooneArb'.

The new *Magnolia* tree originated from an open-pollination in Columbus, Ohio, in 2010 of an unnamed selection of *Magnolia grandiflora*, not patented, as the female, or seed, parent with an unknown selection of *Magnolia grandiflora* as the male, or pollen, parent. The new *Magnolia* tree was discovered and selected by the Inventor as a single plant from within the progeny of the stated open-pollination in a controlled environment in Union, Ky. in 2012.

Asexual reproduction of the new *Magnolia* tree by rooting cuttings in a controlled environment in Hamilton, Ohio has shown that the unique features of this new *Magnolia* tree are stable and reproduced true to type in successive generations.

SUMMARY OF THE INVENTION

Trees of the new *Magnolia* have not been observed under all possible environmental and cultural conditions. The phenotype may vary somewhat with variations in environmental conditions such as temperature and light intensity without, however, any variance in genotype.

The following traits have been repeatedly observed and are determined to be the unique characteristics of 'BooneArb'. These characteristics in combination distinguish 'BooneArb' as a new and distinct *Magnolia* tree:

1. Upright and uniformly pyramidal tree form.
2. Freely branching habit with numerous lateral branches providing a full and densely foliated appearance.
3. Large glossy dark green-colored leaves.
4. Large white-colored flowers that are highly fragrant.
5. Good landscape performance and superior cold hardiness.

Trees of the new *Magnolia* can be compared to trees of the female parent selection. Trees of the new *Magnolia* differ primarily from trees of the female parent selection in the following characteristics:

1. Trees of the new *Magnolia* are upright and uniformly pyramidal in overall form with a dominant central leader whereas trees of the female parent selection have multiple leaders and are less uniform than trees of the new *Magnolia.*
2. Trees of the new *Magnolia* have larger leaves than trees of the female parent selection.
3. Trees of the new *Magnolia* have larger flowers than trees of the female parent selection.

Trees of the new *Magnolia* can be compared to trees of *Magnolia grandiflora* 'Brackens Brown Beauty', disclosed in U.S. Plant Pat. No. 5,520. In side-by-side comparisons, trees of the new *Magnolia* and 'Brackens Brown Beauty' differ primarily in the following characteristics:

1. Trees of the new *Magnolia* have larger leaves than trees of 'Brackens Brown Beauty'.
2. Trees of the new *Magnolia* have larger flowers than trees of 'Brackens Brown Beauty'.
3. Trees of the new *Magnolia* are more cold hardy than trees of 'Brackens Brown Beauty'.

Trees of the new *Magnolia* can also be compared to trees of *Magnolia grandiflora* 'Edith Bogue', not patented. In side-by-side comparisons, trees of the new *Magnolia* and 'Edith Bogue' differ primarily in the following characteristics:

1. Trees of the new *Magnolia* are denser than and not as open as trees of 'Edith Bogue'.
2. Trees of the new *Magnolia* have larger leaves than trees of 'Edith Bogue'.
3. Trees of the new *Magnolia* are more cold hardy than trees of 'Edith Bogue'.

BRIEF DESCRIPTION OF THE PHOTOGRAPHS

The accompanying colored photographs illustrate the overall appearance of the new *Magnolia* tree showing the colors as true as it is reasonably possible to obtain in colored reproductions of this type. Colors in the photographs may differ slightly from the color values cited in the detailed botanical description which accurately describe the colors of the new *Magnolia* tree grown in an outdoor nursery.

The photograph on the first sheet (FIG. 1) is a side perspective view of a typical mature tree of 'BooneArb'.

Figure 2:
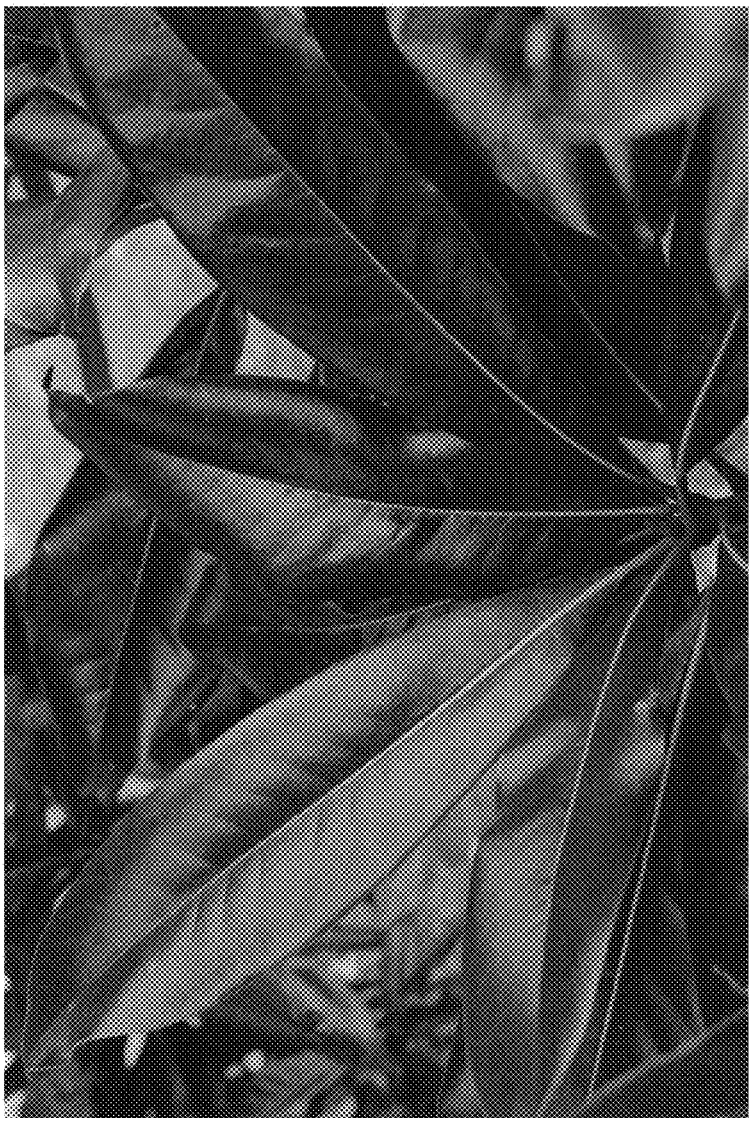

The photograph on the second sheet (FIG. 2) is a close up view of typical leaves of 'BooneArb'.

Figure 3:
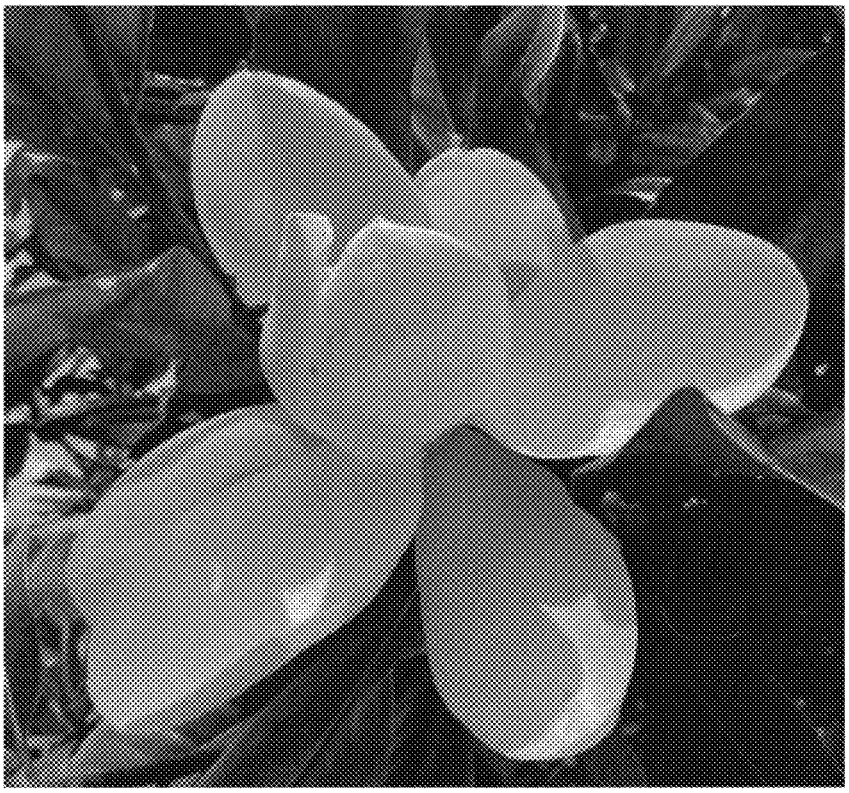

The photograph on the third sheet (FIG. 3) is a side perspective view of a typical flower of 'BooneArb'.

Figure 4:
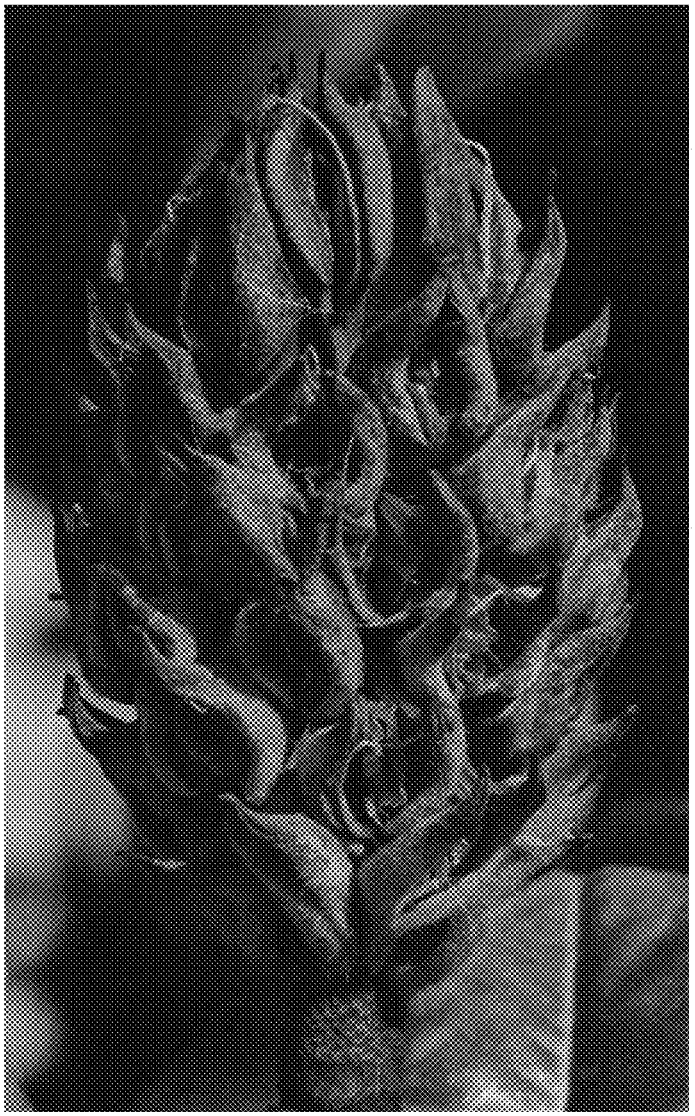

The photograph on the fourth sheet (FIG. 4) is a side perspective view of a typical fruit of 'BooneArb'.

DETAILED BOTANICAL DESCRIPTION

The aforementioned photographs and following observations, measurements and values describe trees grown throughout the year in an outdoor nursery in Union, Ky. and under cultural practices typical of commercial *Magnolia* tree production. Trees used in the photographs and description were nine years old. During the production of the trees, day temperatures ranged from about −1° C. to about 10° C. and night temperatures ranged from about −6° C. to about 4° C. In the following description, color references are made to The Royal Horticultural Society Colour Chart, 2007 Edition, except where general terms of ordinary dictionary significance are used.

Botanical classification: *Magnolia grandiflora* 'BooneArb'.

Parentage:

*Female, or seed, parent.*—Unnamed selection of *Magnolia grandiflora*, not patented.

*Male, or pollen, parent.*—Unknown selection of *Magnolia grandiflora*, not patented.

Propagation:

*Type.*—By cuttings; plants of the new *Magnolia* tree can also be propagated by grafting scions of the new *Magnolia* tree onto named or unnamed selections of *Magnolia grandiflora* rootstock.

*Time to initiate roots during the summer.*—About 60 days at temperatures about 26° C.

*Time to produce a rooted young plant during the summer.*—About 90 days at temperatures about 26° C.

*Root description.*—Medium in thickness, fleshy; typically close to N200A in color, actual color of the roots is dependent on substrate composition, water quality, fertilizer type and formulation, substrate temperature and physiological age of roots.

*Rooting habit.*—Moderately freely; medium density.

Tree description:

*Tree form and growth habit.*—Evergreen tree; upright and uniform pyramidal tree form; horizontal and freely branching habit with numerous lateral branches developing per tree; full and densely-foliated appearance; vigorous to moderately vigorous growth habit and moderate growth rate.

*Tree height.*—About 8.83 meters.

*Tree width* (*spread*).—About 5.49 meters.

*Trunk caliper.*—About 13.34 cm.

*Growth rate, height.*—About 91 cm per year.

*Branch length.*—About 2.89 meters.

*Branch diameter.*—About 5 cm.

*Branch internode length.*—About 7.5 mm on one-year old wood.

*Branch angle orientation.*—Mostly horizontal, about 60° from vertical.

*Branch strength.*—Moderately strong.

*Branch texture and luster.*—Sparsely fissured with horizontal lenticels that are oval in shape; matte.

*Branch color.*—Close to 201D.

*Immature bark texture and luster.*—Pubescent; matte.

*Mature bark texture and luster.*—Glabrous, coarse; matte.

*Immature bark color.*—Close to 200A; at the internodes, close to N144A.

*Mature bark color.*—Close to 197B.

Leaf description:

*Arrangement.*—Alternate, simple.

*Length.*—Relatively long, about 27 cm.

*Width.*—About 9 cm.

*Shape.*—Ovate.

*Apex.*—Acuminate.

*Base.*—Cuneate.

*Margins.*—Entire.

*Venation pattern.*—Pinnate.

*Texture and luster, upper surface.*—Smooth, glabrous; glossy.

*Texture and luster, lower surface.*—Pubescent; matte.

*Color.*—When developing, upper surface: Close to N137A. When developing, lower surface: Close to 152A. Fully developed, upper surface: Close to N137A; venation, close to 147B; color does not change in the autumn. Fully developed, lower surface: Close to 151D; venation, close to 152D, color does not change in the autumn.

*Petioles.*—Length: About 2.54 cm. Diameter: About 4 mm. Strength: Strong. Texture and luster, upper and lower surfaces: Pubescent; matte. Color, upper surface: Close to N199C. Color, lower surface: Close to 199A.

Flower description:

*Flower arrangement and habit.*—Large solitary flowers with numerous flowers developing per tree during the flowering season; flowers face mostly upright.

*Fragrance.*—Highly fragrant; sweet, pleasant.

*Natural flowering season.*—Plants of the new *Magnolia* flower during May and June in northern Kentucky.

*Flower longevity.*—Individual flowers last about three days on the plant; flowers persistent.

*Flower diameter.*—About 24 cm.

*Flower length* (*depth*).—About 14 cm.

*Flower buds.*—Length: About 7 cm. Diameter: About 3 cm. Shape: Bulbous and tapered. Texture: Pubescent. Color: Close to 144B.

*Petals.*—Quantity and arrangement: About nine petals arranged in two whorls. Length: About 15 cm. Width: About 7.5 cm. Shape: Broadly ovate and concave. Apex: Obtuse. Base: Sagittate. Margin: Entire; not undulate. Texture, upper and lower surfaces: Smooth, glabrous. Luster, upper and lower surfaces: Matte. Color: When opening, upper and lower surfaces: Close to NN155B. Fully opened, upper and lower surfaces: Close to NN155B; color does not change with subsequent development.

*Sepals.*—Quantity and arrangement: Two sepals, opposite. Length: About 5 cm. Width: About 3.5 cm. Shape: Ovate. Apex: Acute. Base: Sagittate. Margin: Entire. Texture, upper and lower surfaces: Smooth, glabrous. Luster, upper and lower surfaces: Matte. Color: When opening and fully opened, upper surface: Close to 146D. When opening and fully opened, lower surface: Close to 152B.

*Peduncles.*—Length: About 3 cm. Diameter: About 1 cm. Strength: Strong. Aspect: Upright. Texture: Pubescent. Luster: Matte. Color: Close to N199D.

*Reproductive organs.*—Stamens: Quantity: About 100 per flower. Filament color: Close to 8C. Anther length: About 2 cm. Anther shape: Linear. Anther color: Close to 8C. Pollen amount: Moderate. Pollen color: Close to 8C. Pistils: Style color: Close to 145B. Stigma diameter: About 2.5 cm. Stigma shape: Round. Stigma color: Close to 11A. Fruits: Type: Follicetum. Quantity per plant: About 200 fruits develop per plant during the summer; each fruit with about 50 reddish orange-colored seeds. Length: About 8 cm. Diameter: About 5 cm. Shape: Ovoid. Texture and luster: Rough; matte. Color: Close to 200A.

Temperature tolerance: Trees of the new *Magnolia* have been observed to have superior cold tolerance, tolerating sustained temperatures ranging from −28° C. to 37° C. and to be suitable for USDA Hardiness Zones 5 to 9.

Pathogen & pest tolerance: To date, trees of the new *Magnolia* have been not been observed to be tolerant to pathogens and pests common to *Magnolia* trees.

It is claimed:

1. A new and distinct *Magnolia* tree named 'BooneArb' as illustrated and described.

* * * * *